(12) United States Patent
Held et al.

(10) Patent No.: US 6,222,096 B1
(45) Date of Patent: Apr. 24, 2001

(54) PROMOTER AND CONSTRUCT FOR PLANT TRANSFORMATION

(75) Inventors: Bruce Marvin Held; Herbert Martin Wilson, both of Ames, IA (US)

(73) Assignee: Stine Biotechnology, Ames, IA (US)

( * ) Notice: Subject to any disclaimer, the term of this patent is extended or adjusted under 35 U.S.C. 154(b) by 0 days.

(21) Appl. No.: 09/259,282

(22) Filed: Mar. 1, 1999

(51) Int. Cl.$^7$ ............... C12N 5/04; C12N 15/09; C12N 15/29; C12N 15/82; C12N 15/90

(52) U.S. Cl. ............ 800/278; 435/69.1; 435/320.1; 435/418; 435/419; 435/468; 536/24.1; 800/279; 800/286; 800/290; 800/298; 800/300; 800/301; 800/302

(58) Field of Search ................ 435/320.1, 410, 435/419, 468, 418, 440; 536/24.1, 23.6; 800/278, 279, 286, 288, 295, 298, 300, 301, 302

(56) References Cited

U.S. PATENT DOCUMENTS

| | | | |
|---|---|---|---|
| 5,106,739 | 4/1992 | Comai et al. | 800/278 |
| 5,268,526 | 12/1993 | Hershey et al. | 800/290 |
| 5,290,924 | 3/1994 | Last et al. | 536/24.1 |
| 5,322,938 | 6/1994 | McPherson et al. | 536/24.1 |
| 5,352,605 | 10/1994 | Fraley et al. | 800/278 |
| 5,633,363 | 5/1997 | Colbert et al. | 536/24.1 |
| 5,659,026 | 8/1997 | Baszczynski | 536/24.1 |
| 5,710,267 | 1/1998 | Ellis et al. | 536/24.1 |
| 5,824,857 | 10/1998 | Beachy et al. | 800/278 |

*Primary Examiner*—Paula Hutzell
*Assistant Examiner*—Ashwin D. Mehta
(74) *Attorney, Agent, or Firm*—Rothwell, Figg, Ernst & Manbeck, P.C.

(57) ABSTRACT

The present invention is directed to a promoter, designated MuA. The present invention is also directed to DNA molecules including said promoter, such as a DNA construct comprising the promoter operably linked to one or more genes or antisense DNA. The invention is further directed to transformed plant tissue including the DNA molecule and to transformed plants and seeds thereof. The promoter is useful for driving gene or antisense expression for the purpose of imparting agronomically useful traits such as, but not limited to, increase in yield, disease resistance, insect resistance, herbicide tolerance, drought tolerance and salt tolerance in plants.

35 Claims, 4 Drawing Sheets

(1 of 4 Drawing Sheet(s) Filed in Color)

```
             |----------------------A----------------------|-------
  1  TCAAATTTTT CTCCAGTTCT AAATATCCGG AAACCTCTTG GGATGCCATT

------B--------|-----------------C--------------|---D---
 51  GCCCATCTAT CTGTAATTTA TTGACGAAAT AGACGAAAAG GAAGGTGGCT

-|--------------E----------------|----------F---------|
101  CCTATAAAGC ACATCATTGC GATAACAGAA AGGCCATTGT TGAAGATACC

|-------G--------|----------------H-----------------|-----
151  TCTGCTGACA TTGGTCCCCA AGTGGAAGCA CCACCCCATG AGGAGCACCG

--F--|-----------------G---------------|----------I--------
201  TGGAGTAAGA AGACGTTCGA GCCACGTCGA AAAGCAAGT GTGTTGATGT

----|-------J---------|------------K----------|------L-----
251  AGTATCTCCA TTGACGTAAG GGATGAACAA CAATCCAACT ATCCATCGCA

-----------|------------M--------------|----L-----|--N-
301  AGACCATTGC TCTATATAAG AAAGTTAATA TCATTTCGAG TGGCCACGCT

|
351  G           [SEQ ID NO:1]
```

FIG. 1

```
  1  TCAAATTTTT CTCCAGTTCT AAATATCCGG AAACCTCTTG GGATGCCATT

51  GCCCATCTAT CTGTAATTTA TTGACGAAAT AGACGAAAAG GAAGGTGGCT

101  CCTATAAAGC ACATCATTGC GATAACAGAA AGGCCATTGT TGAAGATACC

151  TCTGCTGACA TTGGTCCCCA AGTGGAAGCA CCACCCCATG AGGAGCACCG

201  TGGAGTAAGA AGACGTTCGA GCCACGTCGA AAAGCAAGT GTGTTGATGT

251  AGTATCTCCA TTGACGTAAG GGATGACGCA CAATCCAACT ATCCATCGCA

301  AGACCATTGC TCTATATAAG AAAGTTAATA TCATTTCGAG TGGCCACGCT

351  G          [SEQ ID NO:2]
```

FIG. 2

```
  1  TCAAATTTTT  CTCCAGTTCT  AAATATCCGG  AAACCTCTTG  GGATGCCATT
     | | | ||||  |  ||       ||||||  |  ||||||| |  ||||  |||||
     TGAGACTTTT  CAACAAAGGG  TAATATCGGG  AAACCTCCTC  GGATTCCATT

51  GCCCATCTAT  CTGT-AATTT  ATTGACGAAA  TAGACGAAAA  GGAAGGTGGC
     ||||| ||||  |||| |  ||  ||  |   |    ||  |||||  ||||||||||
     GCCCAGCTAT  CTGTCACTTC  ATCAAAGGA   CAGTAGAAAA  GGAAGGTGGC

101  TCCTATAAAG  CACATCATTG  CGATAACAGA  AAGGCCATTG  TTGAAGATAC
     ||||  |||   ||||||||||  ||||||  ||  ||||| || |  || ||||||  |
     ACCTACAAAT  GCCATCATTG  CGATAAGGA   AAGGCTATCG  TTCAAGATGC

151  CTCTGCTGAC  ATTGGTCCCC  AAGTGGAAGC  ACCACCCCAT  GAGGAGCACC
     |||||| |||  | ||||||||  |||  | |    |||  ||||  ||||||||| |
     CTCTGCCGAC  AGTGGTCCCA  AAGATGGACC  CCCA-CCCAC  GAGGAGCATC

201  GTGGAGTAAG  AAGACGTTCG  AGCCACGTCG  AAAAAGCAAG  TGTGTTGATG
     |||||  |||  ||||||||||  | |||||||   ||||||||| ||  ||||||
     GTGGAAAAAG  AAGACGTTCC  AACCACGTCT  TCAAAGCAAG  TGGATTGATG

251  TAGTATCTCC  ATTGACGTAA  GGGATGACGC  ACAATCCAAC  TATCCATCGC
     |  ||||||||  |  ||||||||||  ||||||||||  |||||||| ||  |||||  ||||
     TCATATCTCC  ACTGACGTAA  GGGATGACGC  ACAATCCCAC  TATCCTTCGC

301  AAGACCATTG  CTCTATATAA  GAAAGTTAAT  ATCATTTCGA  GTGGCCACGC
     ||||||  ||  ||||||||||  |  |||||| ||  |||||| ||  |  ||  |||||
     AAGACCCTTC  CTCTATATAA  GGAAGTTCAT  TTCATTTGGA  GAGGACACGC

351  TG          [SEQ ID NO:2]
     ||
     TG          [SEQ ID NO:3]
```

PROMOTER AND CONSTRUCT FOR PLANT TRANSFORMATION

BACKGROUND OF THE INVENTION

The present invention is directed to a promoter, designated MuA, with less than 80% homology to a promoter of known activity. The construction of this promoter provides a general method for the discovery of novel sequences with utility as promoters. The present invention is also directed to DNA molecules including said promoter, such as a DNA construct comprising the promoter operably linked to one or more genes or antisense DNA. The invention is further directed to transformed plant tissue including the DNA molecule and to transformed plants and seeds thereof. The promoter is useful for driving gene or antisense expression for the purpose of imparting agronomically useful traits such as, but not limited to, increase in yield, disease resistance, insect resistance, herbicide tolerance, drought tolerance and salt tolerance in plants.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The selection of a promoter in the genetic engineering of a heterologous gene is often a critical factor in obtaining expression of the desired gene. Promoters are typically found at the 5' end of a gene which is either directly or indirectly recognized and bound by a DNA-dependent RNA polymerase during the initiation of transcription of the gene. Consequently promoters play a major role in regulating gene expression. There are three general classes of promoters used in the genetic engineering of plants: 1) tissue specific promoters, 2) inducible promoters, and 3) constitutive promoters. Tissue specific or organ specific promoters drive gene expression in a certain tissue such as in the kernel, root, leaf, or tapetum of the plant. Chemicals or environmental stimuli such as heat, cold, wounding, and etc., induce inducible promoters. Although tissue specific and inducible promoters are required for certain applications, constitutive promoters are the most widely used promoters in the industry. Constitutive promoters are capable of driving a relatively high level of gene expression in most of the tissues of a plant. Constitutive promoters are particularly useful for producing herbicide tolerant plants. The most widely used constitutive promoter in the genetic engineering of plants is the CaMV 35S promoter; other constitutive promoters include the maize polyubiquitin promoter and the rice actin promoter. In general, those familiar with the art agree that constitutive promoters that drive a high level of heterologous gene expression in most of the tissues of a plant are few in number and are of considerable value in the field of genetic engineering of crop plants.

Thus, it is desired to develop additional constitutive promoters for use in plant transformation.

SUMMARY OF THE INVENTION

It is an object of the present invention to provide a strong, constitutive promoter which can effect high level expression of an operably linked gene or antisense DNA in transformed plants.

Accordingly, in one aspect of the present invention, a novel promoter, designated MuA, comprising a nucleotide sequence as set forth in SEQ ID NO:2 is provided.

In another aspect of the invention, a DNA molecule is provided which comprises the MuA promoter operably linked to one or more genes or antisense DNA. The gene or antisense DNA impart an agronomically useful trait or selectable marker to a transformed plant. In one embodiment, the DNA molecule also includes an additional nucleotide sequence that influences gene expression. In a second embodiment, the DNA molecule is part of an expression vector. In a third embodiment, the DNA molecule is part of a transformation vector.

In an additional aspect of the present invention, transformed plant cells and tissues, transformed plants and seeds of transformed plants are provided. The expression of the gene or antisense DNA is regulated by the MuA promoter, and, if present, a second regulatory sequence.

In a further aspect of the invention, a method for obtaining novel sequences with utility as promoters is provided. The method involves the replacement of parts of the sequence of known or newly discovered promoters while maintaining or improving the activity of the promoter.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 1 shows the nucleotide sequence, including all 351 base pairs of the "yeast homolog" to the CaMV 35S promoter. The source and GenBank accession of each homologous sequence from which a given segment is mostly comprised is as follows: A: SC13OKBXV (X94335); B: SCE6592 (U18813); C: SCLACHXII (X94607); D: SC40KBRXVJ (S95720); E: YSCH9315 (U00059); F: YSCCHRVIN (D50617); G: SCCHRIII (X59720); H: SX9571X (Z49810); I: YSCP9659 (U40829); J: SCYBR223C (Z36092); K: EPFCPCG (M81884); L: YSCF6552A (D31600); M: VSCH9177 (U00029); N: CaMV62 (V00141)[CaMV35S—U.S. Pat. No. 532,605]. The three bases that were later changed by site directed mutation to that of the CaMV 35S sequence are underlined.

FIGS. 4(A–B) presents a comparison of GUS expression resulting from transiently expressing the gus gene in plasmids p350096 (FIG. 4A) and pMuA0096 (FIG. 4B).

SUMMARY OF THE SEQUENCES

SEQ ID NO:1 is the sequence of a composite yeast homolog promoter sequence. SEQ ID NO:2 is the sequence of the MuA promoter. SEQ ID NO:3 is the sequence of a CaMV 35S promoter.

DETAILED DESCRIPTION OF THE INVENTION

The present invention is directed to a promoter, designated MuA. The present invention is also directed to DNA molecules including said promoter, such as a DNA construct comprising the promoter operably linked to one or more genes or antisense DNA. The invention is further directed to transformed plant tissue including the DNA molecule and to transformed plants and seeds thereof. The promoter is useful for driving gene or antisense expression for the purpose of imparting agronomically useful traits such as, but not limited to, increase in yield, disease resistance, insect resistance, herbicide tolerance, drought tolerance and salt tolerance in plants.

The present invention is also directed to a general method for obtaining promoters in which sequences of known effect in a promoter are replaced with different sequences over their length. It has been found that hybrid promoters can be constucted with over 15% of the original promoter sequence replaced. The activity of the original promoter is at least maintained or improved.

In accordance with the present invention, the promoter MuA is constructed having less than 85% homology with a promoter of known activity. The construction of this promoter provides an example of a more general method for obtaining promoters in which sequences with known effect are replaced with different sequences over their length while maintaining or improving the known effect. It has been found that hybrid promoters can be constucted with over 15% of the original promoter sequence replaced. This approach is particularly useful with known constitutive promoters of broad utility in a range of species and with promoters obtained from species other than the species to be genetically engineered. The success of this approach, as exemplified with the construction of MuA, is surprising in that promoters generally are thought to be precisely constructed and to be intolerant of modifications without substantial loss of activity.

In the description that follows, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. For example, a promoter may be regulated in a tissue-specific manner such that it is only active in transcribing the associated coding region in a specific tissue type(s) such as leaves, roots or meristem.

In contrast, the rate of transcription is not generally regulated by an inducing agent if the promoter is a constitutive promoter. The promoter may be tissue-general, also known as non-tissue-preferred, such that it is active in transcribing the associated coding region in a variety of different tissue types.

A core promoter contains essential nucleotide sequences for promoter function, including the TATA box and start of transcription. By this definition, a core promoter may or may not have detectable activity in the absence of specific sequences that may enhance the activity.

An isolated DNA molecule is a fragment of DNA that is not integrated in the genomic DNA of an organism.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

To operably link one nucleotide sequence to another refers to joining two DNA fragments to produce a chimeric DNA construct that has biological activity. For example, an isolated DNA fragment comprising a promoter, such as the MuA promoter, is operably linked to an isolated DNA fragment comprising a structural gene or antisense DNA. The resulting chimeric DNA construct is functional when the MuA promoter is shown to initiate transcription of the structural gene or antisense DNA.

The term expression refers to the biosynthesis of a gene product. For example, in the case of a structural gene, expression involves transcription of the structural genes into mRNA and the translation of mRNA into one or more polypeptides. In the case of antisense DNA, expression involves transcription of the antisense DNA into an antisense RNA.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene or antisense DNA that is expressed in a host cell. Typically, gene expression is placed under the control of certain regulatory elements, including constitutive or inducible promoters, tissue-specific regulatory elements, and enhancers. Such a gene or antisense DNA is said to be "operably linked to" the regulatory elements.

A foreign gene refers in the present description to a DNA sequence that is operably linked to at least one heterologous regulatory element.

A recombinant host may be any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

A transgenic plant is a plant having one or more plant cells that contain a structural gene or antisense DNA operably linked to the MuA promoter.

In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA. The RNA transcript is termed an antisense RNA, and a DNA sequence that encodes the antisense RNA is termed an antisense gene. Antisense RNA molecules are capable of binding to mRNA molecules, resulting in an inhibition of mRNA translation.

An antisense nucleic acid (oligonucleotide) is a nucleic acid (oligonucleotide) which has a sequence exactly opposite to an mRNA molecule made in an organism. Messenger RNA molecules made in an organism serve as templates for the synthesis of protein. Since the "antisense" mRNA molecule binds tightly to its mirror image, it can prevent a particular protein from being made.

In one aspect of the present invention, a novel promoter, designated MuA, comprising a nucleotide sequence as set forth in SEQ ID NO:2 is provided.

In another aspect of the invention, a DNA molecule is provided which comprises the MuA promoter operably linked to one or more genes or antisense DNA. The gene or antisense DNA imparts an agronomically useful trait or selectable marker to a transformed plant. In one embodiment, the DNA molecule also includes an additional nucleotide sequence that influences gene expression. Examples of nucleotide sequences that influence the regulation of heterologous genes include enhancers or activating regions, such as those derived from CaMV 35S, opine synthase genes or other plant genes (U.S. Pat. Nos. 5,106,739; 5,322,938; 5,710,267; 5,268,526; 5,290,294). In a second embodiment, the DNA molecule is part of an expression vector. In a third embodiment, the DNA molecule is part of a transformation vector.

In an additional aspect of the present invention, transformed plant cells and tissues, transformed plants and seeds of transformed plants are provided. The expression of the gene or antisense DNA is regulated by the MuA promoter and second regulatory sequence, if present.

By means of the present invention, agronomic genes and selectable marker genes can be operably linked to the MuA promoter and constitutively expressed in transformed plants. More particularly, plants can be genetically engineered to express various phenotypes of agronomic interest. Such genes included, but are not limited to, those described herein.

1. Genes That Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium fulvum* (Jones et al., 1994), tomato Pto gene, which encodes a protein kinase, for resistance to *Pseudomonas syringae* pv. tomato (Martin et al., 1993), and Arabidopsis RSSP2 gene for resistance to *Pseudomonas syringae* (Mindrinos et al., 1994).

(B). A *Bacillus thuringiensis* protein, a derivative thereof or a synthetic polypeptide modeled thereon, such as, a nucleotide sequence of a Bt δ-ndotoxin gene (Geiser et al., 1986). Moreover, DNA molecules encoding δ-endotoxin genes can be purchased from American Type Culture Collection (Rockville, Md.), under ATCC accession numbers. 40098, 67136, 31995 and 31998.

(C) A lectin, such as, nucleotide sequences of several *Clivia miniata* mannose-binding lectin genes (Van Damme et al., 1994).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include, a rice cysteine proteinase inhibitor (Abe et al., 1987), a tobacco proteinase inhibitor I (Huub et al., 1993), and an α-amylase inhibitor Sumitani et al., 1993).

(F) An insect-specific hormone or pheromone such as an ecdysteroid and juvenile hormone a variant thereof, a mimetic based thereon, or an antagonist or agonist thereof, such as, baculovirus expression of cloned juvenile hormone esterase, an inactivator of juvenile hormone (Hammock et al., 1990).

(G) An insect-specific peptide or neuropeptide which, upon expression, disrupts the physiology of the affected pest. Examples of such genes include, an insect diuretic hormone receptor (Regan, 1994), an allostatin identified in *Diploptera puntata* (Pratt, 1989), insect-specific, paralytic neurotoxins (U.S. Pat. No. 5,266,361).

(H) An insect-specific venom produced in nature by a snake, a wasp, etc., such as, a scorpion insectotoxic peptide (Pang, 1992).

(I) An enzyme responsible for a hyperaccumulation of monterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993) and parsley ubi4-2 polyubiquitin gene (Kawalleck et al., 1993).

(K) A molecule that stimulates signal transduction. Examples of such molecules include, nucleotide sequences for mung bean calmodulin cDNA clones (Botella et al., 1994) a nucleotide sequence of a maize calmodulin cDNA clone (Griess et al., 1994).

(L) A hydrophobic moment peptide. See U.S. Pat. Nos. 5,659,026 and 5,607,914, the latter teaches synthetic antimicrobial peptides that confer disease resistance.

(M) A membrane permease, a channel former or a channel blocker, such as, a cecropin-β lytic peptide analog (Jaynes et al., 1993) which renders transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990).

(O) An insect-specific antibody or an immunotoxin derived therefrom. Thus, an antibody targeted to a critical metabolic function in the insect gut would inactive an affected enzyme, killing the insect. For example, Taylor et al. (1994) shows enzymatic inactivation in transgenic tobacco via production of single-chain antibody fragments.

(P) A virus-specific antibody. See, for example, Tavladoraki et al. (1993), which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992). The cloning and characterization of a gene which encodes a bean endopolygalacturonase-inhibiting protein is described by Toubart et al. (1992).

(R) A developmental-arrestive protein produced in nature by a plant, such as, the barley ribosome-inactivating gene have an increased resistance to fungal disease (Longemann et al., 1992).

2. Genes That Confer Resistance to a Herbicide (A) A herbicide that inhibits the growing point or meristem, such as an imidazalinone or a sulfonylurea.

Exemplary genes in this category code for mutant ALS (Lee et al., 1988) and AHAS enzyme (Miki et al., 1990).

(B) Glyphosate (resistance imparted by mutant EPSP synthase and aroA genes, respectively) and other phosphono compounds such as glufosinate (PAT and bar genes), and pyridinoxy or phenoxy proprionic acids and cyclohexones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al. (1989) describes the production of transgenic plants that express chimeric bar genes coding for phosphinothricin acetyl transferase activity. Exemplary of genes conferring resistance to phenoxy proprionic acids and cyclohaexones, such as sethoxydim and haloxyfop, are the Accl-S1, Accl-S2 and Accl-S3 genes described by Marshall et al. (1992).

(C) A herbicide that inhibits photosynthesis, such as a triazine (psbA and gs+ genes) and a benzonitrile (nitrilase gene). Przibilla et al. (1991) describes the use of plasmids encoding mutant psbA genes to transform Chlamydomonas. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al. (1992).

3. Genes That Confer or Contribute to a Value-Added Trait (A) Modified fatty acid metabolism, for example, by transforming maize or Brassica with an antisense gene or stearoyl-ACP desaturase to increase stearic acid content of the plant (Knultzon et al., 1992).

(B) Decreased phytate content
  (1) Introduction of a phytase-encoding gene would enhance breakdown of phytate, adding more free phosphate to the transformed plant, such as the *Aspergillus niger* phytase gene (Hartingsveldt et al., 1993).
  (2) A gene could be introduced that reduces phytate content. In maize, this, for example, could be accomplished, by cloning and then reintroducing DNA associated with the single allele which is responsible for maize mutants characterized by low levels of phytic acid (Raboy et al., 1990).

(C) Modified carbohydrate composition effected, for example, by transforming plants with a gene coding for an enzyme that alters the branching pattern of starch. Examples of such enzymes include, *Streptococcus mucus* fructosyl-transferase gene (Shiroza et al., 1988), *Bacillus subtilis* levansucrase gene (Steinmetz et al., 1985), *Bacillus licheniformis* α-amylase (Pen et al., 1992), tomato invertase genes (Elliot et al., 1993), barley amylase gene (Søgaard et al., 1993), and maize endosperm starch branching enzyme II (Fisher et al., 1993).

4. Selectable Marker Genes:

(A) Numerous selectable marker genes are available for use in plant transformation including, but not limited to, neomycin phosphotransferase I, hygromycin phosphotransferase, EPSP synthase and dihydropteroate. See, Miki et al. (1993).

Synthesis of genes suitably employed in the present invention can be effected by means of mutually priming long oligonucleotides. See, for example, Ausubel et al. (1990) and Wosnick et al. (1987). Moreover, current techniques which employ the polymerase chain reaction permit the synthesis of genes as large as 1.8 kilobases in length. See Adang et al. (1993) and Bambot et al. (1993). In addition, genes can readily be synthesized by conventional automated techniques.

In a further aspect of the invention, a method for obtaining novel sequences with utility as promoters is provided. The method involves the replacement of part of the sequence of known or newly discovered promoters while maintaining or improving the activity of the promoters, as demonstrated by the construction of MuA. It has been found that hybrid promoters can be constucted with over 15% of the original promoter sequence replaced.

In accordance with the present invention, a novel promoter is constructed by the following steps. The sequence of a known or newly discovered promoter is compared with known nucleic acid sequences, such as sequences in genomic databases. In one embodiment, this comparison is made in the GenBank database using a program such as FASTA (Genetics Computer Group, Madison, Wis.). Additional suitable databases and comparison programs are known to a person of skill in the art. Segments of sequence similar to the query sequence, i.e., the known or newly discovered promoter, are identified and selected. Segments are considered similar if they have between 60% and 100% sequence identity over the segment being examined. These segments are usually 20–100 bases in length, although smaller or longer segments can also be selected. The selected sequences are aligned in linear order according to the sequence of the promoter being modified. The resultant promoter is a hybrid promoter comprised of sequences similar to but different from the original promoter. The short segments that make up the synthetic hybrid promoter may be parts of promoters or regulatory regions from other genes. The synthetic hybrid promoter is then constructed and empirically tested in a test expression system to determine its quantitative and qualitative characteristics. If the synthetic hybrid promoter has maintained or improved activity, it may be used directly. If the synthetic hybrid promoter has a lower activity, the sequence of the synthetic hybrid promoter is further modified by replacing some of the bases to generate a new hybrid promoter. The new hybrid promoter is again constructed and tested to determine if it has the desired maintained or improved activity. This procedure can be performed as often as necessary to derive the final hybrid promoter having the desired activity.

The method for developing novel promoters in accordance with the present invention is particularly useful in plant biotechnology. There is a general lack of available promoters for use in the production of commercially valuable transgenic plants. In the course of constructing transformation vectors, it is often necessary to use a given promoter multiple times to drive different genes. Those trained in genetic engineering of plants will recognize the undesirability of this circumstance as sequence homology within a vector has been associated with the phenomenon of gene silencing. By using a synthetic hybrid promoter, prepared in accordance with the present invention, the problem of homology-dependent gene silencing can be ameliorated. In order to maximize this effect of the hybrid promoter, it is preferred that over at least 15% of the sequence of the original promoter has been replaced in the hybrid promoter.

EXAMPLES

The present invention is described by reference to the following Examples, which are offered by way of illustration and are not intended to limit the invention in any manner. Standard techniques well known in the art or the techniques specifically described below were utilized. In these Examples, corn is used for illustrative purposes only. Other plant species are also transformed with the DNA constructs of the present invention using techniques well known in the art.

Example 1

Construction of Plasmids Used in Corn Transient Assays

Figure 1:
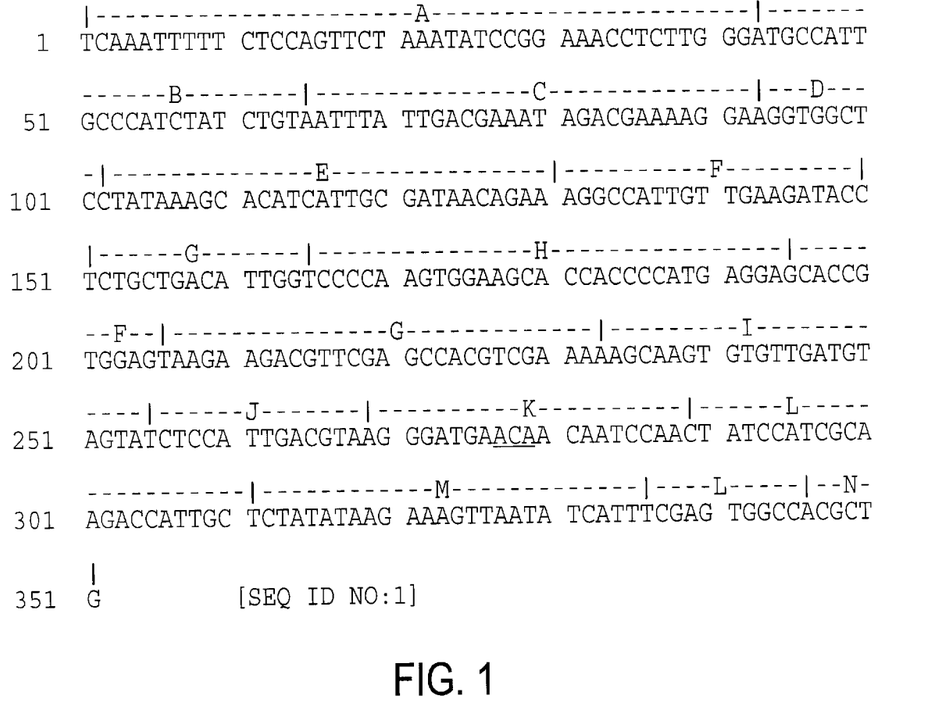

A promoter sequence, designated yeast homolog to the CaMV 35S, was designed with around 80% homology to the CaMV 35S promoter (FIG. 1). The sequence was not randomly derived but based on homologies found in the database at the time of design. Three hundred fifty one bases of the CaMV 35S promoter were compared to plant DNA sequences, which included sequences from yeast, in the database GenBank using the FASTA program. Regions of homologies were then manually aligned using the CaMV 35S promoter as the template. A few bases within segments and in regions linking segments were changed to match the CaMV 35S sequence so that the homology would remain around 80%. FIG. 1 depicts the yeast homolog sequence and the GenBank designations from which the majority of the sequence for a given segment was derived. All of the homologies were from yeast with the exception of segment "K" of FIG. 1 which was from the chloroplast of *Epifagus virginiana* and segment "N" of FIG. 1 which was from CaMV 35S. The sequence was synthesized by the Molecular Biology Group at The Midland Certified Reagent Company, Midland, Texas with EcoRI and SacI compatible overhangs on the 5' and 3' ends, respectively.

Plasmid 350096 was constructed by removing a root preferential promoter with an EcoRI and SacI double digestion from the plasmid pZMOO96 of U.S. Pat. No. 5,633,363 and replacing it with a CaMV 35S promoter from pSLJ4k1 which had compatible EcoRI/SacI cohesive ends. Plasmid pSLJ4k1 was obtained from the Sainsbury Laboratory at the John Innes Center, England. Plasmid 350096 consisted of a 1.3 kb CAMV 35S promoter, 0.5 kb intervening sequence six (IV6) from corn alcohol dehydrogenase, 1.8 kb gus reporter gene, 0.25 kb nopaline syntase 3' end (nos) in a pUC18 backbone.

The CaMV 35S promoter in p350096 was replaced with the synthesized yeast homolog. The plasmid p350096 was digested with EcoRI and SacI, then dephosphorylated to prevent self ligation. The yeast homolog was directionally ligated into the EcoRI and SacI sites to produce pY0096.

Figure 2:
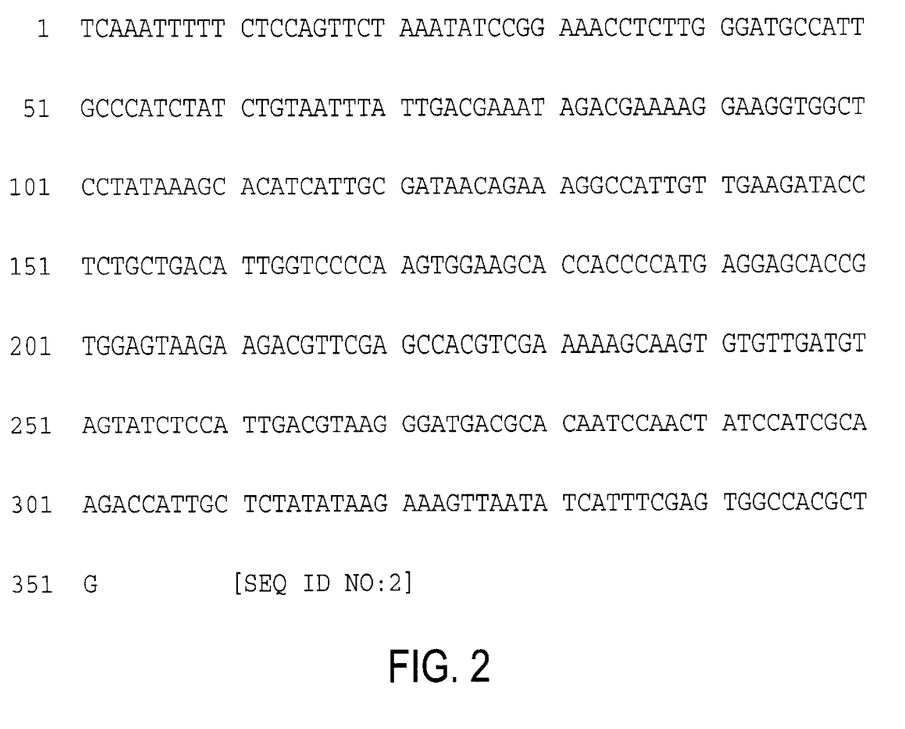
FIG. 2 shows the MuA promoter sequence (SEQ ID NO:2) which resulted after site directed mutatgenesis.
Figure 3:
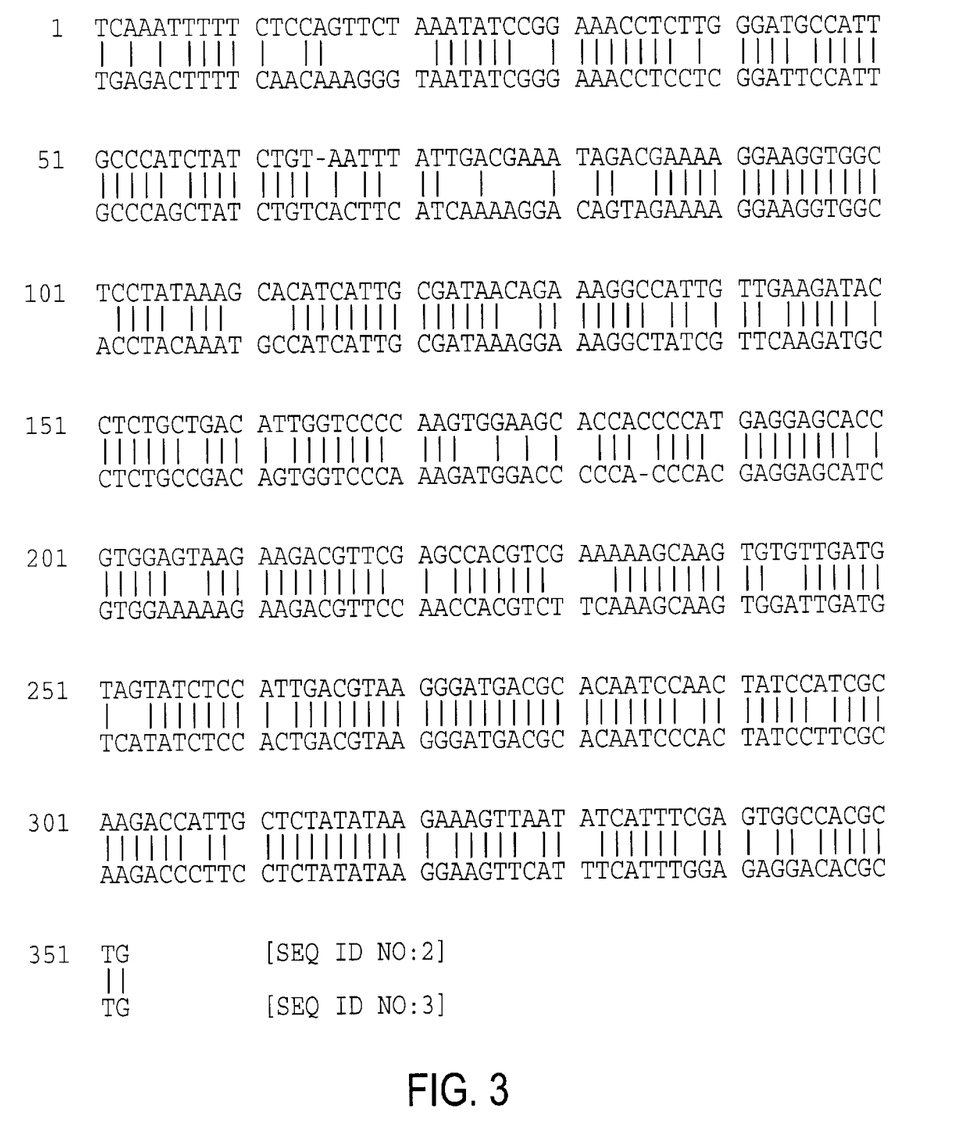
FIG. 3 shows the homology between the MuA and the CaMV 35S promoter sequences (SEQ ID NO:2 and SEQ ID NO:3, respectively) over a 352 bp overlap.

The yeast homolog to the CAMV 35S promoter produced a low level of transient expression when compared to the CaMV 35S promoter in transient expression experiments in corn callus (see Example 2). An increase in the level of expression was sought by changing some nucleotides thought to be important for the function of the CaMV 35S promoter. Three bases at positions 277, 278, and 279 of the yeast homolog (FIG. 1) were changed from ACA to CGC by site directed mutagenesis using the QuikChange™ site-directed mutagenesis kit according to the manufacturer Stratagene (FIG. 1). This new promoter called MuA (FIG. 2) in plasmid pMuAOO96 resulted in a similar level of transient expression in corn callus when compared to the CaMV 35S promoter (see Example 2, FIG. 4). The sequence of MuA (FIG. 2) has 79.5% homology over 352 base overlap to the CaMV 35S promoter published by Gardner et al., 1981. The comparison of the MuA promoter with the CaMV 35 S promoter is shown in FIG. 3.

Example 2

Transient Assays in Corn Callus

Tissue preparation: Type II callus of Stine elite inbred 963 was used as target tissue for transient assays. The Type II callus, initiated from immature embryos on N6AMOD medium (Table 1), was maintained as a stock culture on DN62 medium (Table 1). Tissue was transferred every ten days. For transient assays tissue was taken from these cultures (usually 4 to 5 days after subculture) and spread on a Whatman No 4 filter disk on DN62OSM medium (Table 1) up to one day prior to bombardment with the particle inflow gun.

DNA Delivery: A particle inflow gun (PIG) as described by Finer et al. (1992) and Vain et al. (1993) was used to deliver the DNA. In brief, 50 mg of tungsten particles (M10 from Sylvania Chemicals/Metals, Towanda, Pa.) were sterilized for 15 minutes in 95% ethanol in a 1.5 ml microfuge tube. Particles were rinsed 3 times in sterile distilled water by repeated vortexing, centrifugation and resuspension in 0.5 ml water. Particle suspensions were made fresh for each experiment. Plasmid DNA was coated onto the particles by mixing 25 ul of tungsten particle suspension (2.5 mg), 5 μl of DNA (5 ug), 25 ul of 2.5 M $CaCl_2$, and 10 ul of 100 mM spermidine (free base). After allowing the particles to settle for a few minutes while on ice, 50 ul of supernatant was removed. Two ul of the remaining particle suspension was pipetted onto the center of the screen of a syringe filter unit. The syringe filter unit was reassembled and screwed into the Luer-lok needle adaptor within the chamber. The target tissue in a petri plate was placed about 15 cm below the syringe filter unit. A vacuum of approximately 28 in Hg was applied and the particles were discharged when helium (80 psi) was released following activation of the solenoid by the timer relay.

TABLE 1

Media Compositions

| Ingredients/L | N6AMOD | DN62 | DN62OSM |
|---|---|---|---|
| N6 salts[1] | 3.98 g | 3.98 g | 3.98 g |
| N6 vitamins[2] | 1 ml | 1 ml | 1 ml |
| Asparagine | 150 mg | 800 mg | 800 mg |
| Myo-inositol | 100 mg | 100 mg | 100 mg |
| Proline | 700 mg | 1400 mg | 1400 mg |
| Casamino Acids | | 100 mg | 100 mg |
| 2,4-D | 1 mg | 1 mg | 1 mg |
| Sucrose | 20 g | 20 g | 20 g |
| Glucose | 10 g | | |
| MES | 500 mg | | |
| Mannitol | | | 45.5 g |
| Sorbitol | | | 45.5 g |
| $AgNO_3$ | 10 mg | | |
| Gelrite | 2 g | 3 g | 3 g |
| pH | 6.0 | 5.8 | 5.8 |

[1]N6 salts - Sigma Plant Culture Catalogue ref. C 1416.
[2]N6 vitamins: 2 mg/l glycine, 0.5 mg/l nicotinic acid, 0.5 mg/l pyridoxine HCl, 1 mg/l thiamine HCl (Chu, 1978).

Figure 4A:
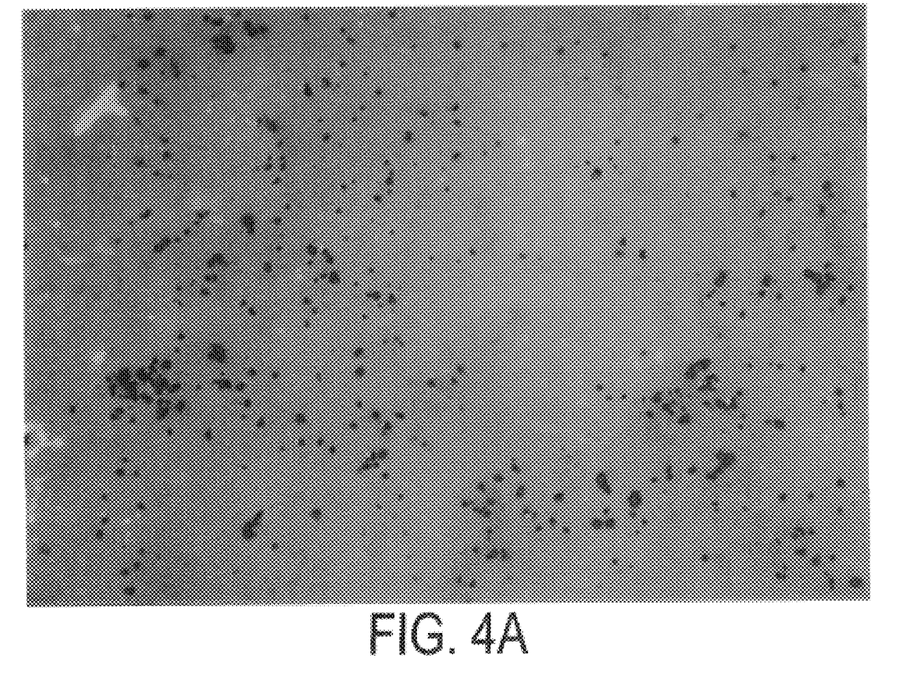
Figure 4B:
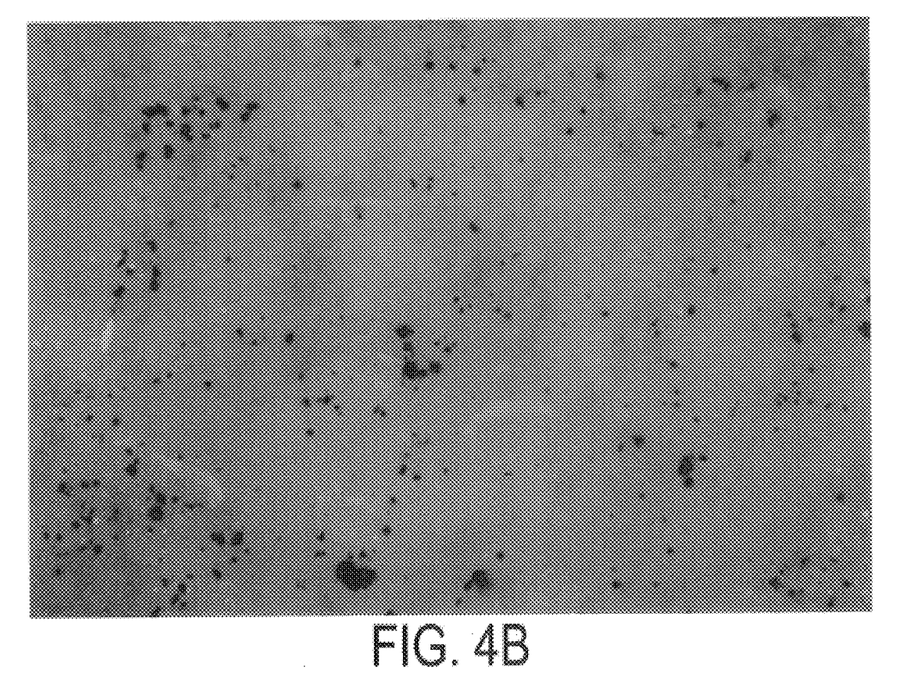

After bombardment, callus was incubated at 25° C. in the dark for 16–24 h on the same medium used for bombardment. Then, transient gus expression was evaluated by incubating the tissue in 0.5 mg/ ml X-gluc (Gold Biotechnology, Inc. St. Louis, Mo.) in 0.1M sodium phosphate buffer pH 7.0 and 0.1% Triton-X-100 at 37° C. for 4–16 h after which the number and intensity of blue foci were evaluated under a stereo microscope at approximately 10× magnification. Tissue was transformed with either p350096, or pMuA0096. Results are shown in FIG. 4. It is seen that tissue transformed with p350096 (FIG. 4A) or pMuA0096 (FIG. 4B) had similar levels of transient expression. Tissue transformed with pY0096 was found to have lower levels of transient expression.

Example 3

Construction of Plasmids Used in the Transformation of Corn

The bar gene in pBARGUS (Fromm et al., 1990) was used to replace the gus gene in pMuA0096 using the BamHI and PstI sites. Briefly, pBARGUS was digested with BamHI and PstI and the 800 bp fragment containing the bar gene was isolated. The plasmid pMuA0096 was digested with BamHI and PstI and the ends were dephosphorylated. The 800 bp fragment containing the bar gene was ligated to the digested, dephosphorylated pMuA0096 to produce the plasmid pMuABar.

The MuABar expression cassette was removed from pMuABar by digestion with EcoRI and HindII and cloned into pSB11 (obtained from Japan Tobacco) after digestion with EcoRI and HindIII and dephosphorylation, resulting in the plasmid pSB11MuABar. Plasmid pSB11MuABar was combined with pSB1 (obtained from Japan Tobacco) via homologous recombination and mobilized into Agrobacterium LBA 4404 via triparental mating according to U.S. Pat. No. 5,591,616 resulting in pSBMuABar. This plasmid in LBA 4404 was used in the transformation of

Example 4

Transformation of Corn

Agrobacterium-mediated DNA delivery was used to produce stable corn transformants carrying MuA driving the bar gene. Agrobacterium LBA 4404 harboring PSB11MuABar recombined with pSB 1 (Example 3) was taken from glycerol stocks and streaked out on YP medium (5 g/l yeast extract, 10 g/l peptone, 5 g/l NaCl, 15 g/l agar and pH 6.8) supplemented with 50 mg/l spectinomycin and grown for one or two days at 28° C.

Immature embryos of Stine elite inbred 963 were aseptically removed from kernels of plants grown in a grow room (15h photoperiod, 28° day and 25° night). Embryos were harvested 10 to 11 days after pollination when they were between 1 mm and 2 mm in length and then placed in 2 ml of LSinf medium (Table 2) in an Eppendorf tube. The mixture was then stirred with a vortex mixer (Vortex Genie 2) at full speed for 5 seconds, the LSinf removed, replaced with fresh medium and then stirred again. All medium was then removed from the tube using a Pasteur pipette. Bacteria were collected with a platinum loop (enough to coat the wire of the loop) and thoroughly suspended in 1 ml of Lsinf-AS medium (Table 2) using a Pasteur pipette. The bacterial suspension was then introduced into the tube containing the embryos and the mixture stirred with a vortex mixer at full speed for 30 seconds. After this the embryos were allowed to stand for five minutes and were then transferred to the surface of LSAS medium (Table 2) solidified with agar, care being taken to remove any accompanying liquid. Embryos were immediately oriented so that the scutellar surface was uppermost.

TABLE 2

Media Compositions

| Ingredients/L | LSAS | Lsinf | LsinfAS |
|---|---|---|---|
| MS salts/vits[1] | 4.43 g | 4.43 g | 4.43 g |
| Proline | 700 mg | | |
| Casamino Acids | | 1.0 g | 1.0 g |
| Na$_2$EDTA | 37.3 mg | 37.3 mg | 37.3 mg |
| 2,4-D | 1.5 mg | 1.5 mg | 1.5 mg |
| MES | 500 mg | | |
| Thiamine HCl | | 1.0 mg | 1.0 mg |
| Sucrose | 20 g | 68.5 g | 68.5 g |
| Glucose | 10 g | 36.0 g | 36.0 g |
| Acetosyringone | | 100 µm | 100 µm |
| Phytagar | 7 g | | |
| pH | 5.8 | 5.2 | 5.2 |

[1]MS salts/vits - Sigma Plant Culture Catalogue ref. M5519

The embryos were then cultured in the dark at 19° for 48 hours. After this time the plates were removed from the incubator and placed at 45° for 30 minutes. Then they were returned to the 19° incubator for a further day. Following this the embryos were transferred to DN62ALC (Table 3) and incubated at 24° for 5 days. Next, the embryos were transferred to DN62ALCB (Table 3) and incubated at 24° for 14 days. For the next 14-day passage the cefotaxime concentration was raised from 50 mg/l (in DN62ALC) to 250 mg/l. This medium—DN62ACB (Table 3)—allowed for a better control of the residual Agrobacterium cells contaminating the corn embryos. Embryos were then transferred back to DN62ALCB for a further 14 days. At this time, transformed corn clones could be recognized by their ability to grow as prolific Type II callus on the bialaphos-containing medium. Culture of the clones continued on DN62B medium (see Table 3) for a further two weeks after which time the Type II callus was transferred to DNROB medium (Table 4) to initiate regeneration. After one to two weeks on DNROB somatic embryos developed as individual structures. These embryos were allowed to mature for one to two weeks on a further passage of DNROB (Table 4) and were then transferred to DNO6S (Table 4). Finally, they were transferred to MSOG or 1/2MS0.1IBA (Table 4) where they germinated and formed plantlets. The plantlets were then transferred to tubes containing 1/2MS 0.1IBA where roots developed. The plants were transferred to peat pots prior to going into the greenhouse. In the greenhouse the plants were grown to maturity and seed collected either after backcrossing to Stine inbred 963 or after selfing.

The presence of an expressing bar gene was then confirmed by leaf painting with the agricultural herbicide, LIBERTY, both in the primary transformants and in progeny. Mendelian ratios of an expressing bar gene were routinely observed in the progeny.

TABLE 3

Media Compositions

| Ingredients/L | DN62B | DN62ALC | DN62ALCB | DN62ACB |
|---|---|---|---|---|
| N6 salts[1] | 3.98 g | 3.98 g | 3.98 g | 3.98 g |
| N6 vitamins[1] | 1 ml | 1 ml | 1 ml | 1 ml |
| Asparagine | 800 mg | 800 mg | 800 mg | 800 mg |
| Myo-inositol | 100 mg | 100 mg | 100 mg | 100 mg |
| Proline | 1400 mg | 1400 mg | 1400 mg | 1400 mg |
| Casamino Acids | 100 mg | 100 mg | 100 mg | 100 mg |
| 2,4-D | 1 mg | 1 mg | 1 mg | 1 mg |
| Sucrose | 20 g | 20 g | 20 g | 20 g |

TABLE 3-continued

Media Compositions

| Ingredients/L | DN62B | DN62ALC | DN62ALCB | DN62ACB |
|---|---|---|---|---|
| Glucose | | 10 g | | |
| AgNO₃ | | 10 mg | 10 mg | 10 mg |
| Bialaphos | 1 mg | | 1 mg | 1 mg |
| Cefotaxime | | 50 mg | 50 mg | 250 mg |
| Gelrite | 3 g | 3 g | 3 g | 3 g |
| pH | 5.8 | 5.8 | 5.8 | 5.8 |

¹N6 salts and vitamins as in Table 1.

TABLE 4

Media Compositions

| Ingredients/L | DNROB | DNO6S | MSOG | ½MS 0.1IBA |
|---|---|---|---|---|
| MS Salts¹ | 4.43 g | 4.43 g | 4.43 g | 2.215 g |
| Asparagine | 800 mg | | | |
| Proline | 1400 mg | | | |
| Na₂EDTA | 37.3 mg | 37.3 mg | 37.3 mg | 37.3 mg |
| Casamino Acids | 100 mg | | | |
| Nicotinic Acid | 0.5 mg | | | |
| Gibberellic Acid | | | 0.1 mg | |
| Indole-3-Butyric Acid | | | | 0.1 mg |
| Sucrose | | 60 g | 30 g | 20 g |
| Sorbitol | 20 g | | | |
| Bialaphos | 1 mg | | | |
| Gelrite | 2 g | 2 g | | |
| Phytagar | | | 7 g | 7 g |
| pH | 5.8 | 5.8 | 5.8 | 5.8 |

¹MS Salts - Sigma Plant culture Catalogue ref. M5519

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Abe et al. (1987). *J. Biol. Chem.* 262:16793.
Adang et al. (1993), *Plant Molec. Biol.* 21:1131.
Ausubel et al. (1990). *Current Protocols in Molecular Biology*, Wiley lnterscience, pp. 8.2.8–8.2.13.
Bambot et al. (1993). *PCR Methods and Applications* 2:266.
Beachy et al. (1990). *Ann. Rev. Phytopathol.* 28:451.
Botella et al. (1994). *Plant Molec. Biol.* 24:757.
Chu C. C. (1978). "The N6 medium and its application to anther culture of cereal crops." In *Proc. Symp. on Plant Tissue Culture.* Sci. Press, Beijing, pp 43–50.
De Greef et al. (1989). *Bio/Technology* 7:61.
Elliot et al. (1993). *Plant Molec. Biol.* 21:515.
Finer, J. J. et al. (1992). *Plant Cell Reports* 11:323–328.
Fisher et al. (1993). *Plant Physiol.* 102:1045.
Fromm, et al. (1990). *Biotechnology* 8:833–839.
Gardner et al. (1991). *Nucl. Acids Res.* 9:2871–2888.
Geiser et al. (1986). *Gene* 48:109.
Griess et al. (1994). *Plant Physiol.* 104:1467.
Hammock et al. (1990). *Nature* 344:458.
Hayes et al. (1992). *Biochem. J.* 285:173.
Huub et al. (1993). *Plant Molec. Biol.* 21:985.
Jaynes et al. (1993). *Plant Sci.* 89:43.
Jones et al. (1994). *Science* 266:789.
Kawalleck et al. (1993). *Plant Molec. Biol.* 21:673.
Knultzon et al. (1992). *Proc. Nat. Acad. Sci. USA* 89:2624.
Kramer et al. (1993). *Insect Molec. Biol.* 23:691.
Lamb et al. (1992). *Bio/Technology* 10:1436.
Lee et al. (1988). *EMBOJ.* 7:1241.
Longemann et al. (1992). *Bio/Technology* 10:3305.
Marshall et al. (1992). *Theor. Appl. Genet.* 83:435.
Martin et al. (1993). *Science* 262:1432.
Miki et al. (1990). *Theor. Appl. Genet.* 80:449.
Miki et al. (1993). "Procedures for Introducing Foreign DNA into Plants," in *Methods in Plant Molecular Biology and Biotechnology*, Glick et al. (eds.), CRC Press, pp. 67–88.
Mindrinos et al. (1994). *Cell* 78:1089.
Pang et al. (1992). *Gene* 116:165.
Pen et al. (1992). *Bio/Technology* 10:292.
Pratt et al. (1989). *Biochem. Biophys. Res. Comm.* 163:1243.
Przibilla et al. (1991). *Plant Cell* 3:169.
Raboy et al. (1990). *Maydica* 35:383.
Regan (1994). *J. Biol. Chem.* 269:9.
Shiroza et al. (1988). *J. Bacteriol.* 170:810.
Søgaard et al. (1993). *J. Biol. Chem.* 268:22480.
Steinmetz et al. (1985). *Mol. Gen. Genel.* 200:220.
Sumitani et al. (1993). *Biosci. Biotech. Biochem.* 57:1243.
Tavladoraki et al. (1993). *Nature* 266:469.
Taylor et al. (1994). Abstract #497, Seventh Int'l. Symposium on Molecular Plant-Microbe Interactions.
Toubart et al. (1992). *Plant J.* 2:367.
Vain, P. et al. (1993). *Plant Cell, Tissue and Organ Culture* 33:237–246.
Van Damme et al. (1994). *Plant Molec. Biol.* 24:825.
Van Hartingsveldt et al. (1993). *Gene* 127:87.
Wosnick et al. (1987). *Gene* 60:115.
U.S. Pat. No. 4,769.061.
U.S. Pat. No. 4,810,648.
U.S. Pat. No. 4,940,835.
U.S. Pat. No. 4,975,374.
U.S. Pat. No. 5,106,739.
U.S. Pat. No. 5,266,317.
U.S. Pat. No. 5,268,526.
U.S. Pat. No. 5,290.294.
U.S. Pat. No. 5,322,938.
U.S. Pat. No. 5,591,616.
U.S. Pat. No. 5,607,914.
U.S. Pat. No. 5,633,363.
U.S. Pat. No. 5,659,026.
U.S. Pat. No. 5,710,267.
PCT published application No. WO 93/02197.
European published application No. 0 242 246.
European published application No. 0 333 033.

---

What is claimed is:

1. An isolated DNA molecule comprising a nucleic acid selected from the group consisting of a nucleic acid comprising a nucleotide sequence as set forth in SEQ ID NO:1 and a nucleic acid comprising a nucleotide sequence as set forth in SEQ ID NO:2.

2. The DNA molecule of claim 1, wherein said nucleic acid comprises a nucleotide sequence as set forth in SEQ ID NO:2.

3. An isolated DNA molecule comprising a first nucleic acid selected from the group consisting of a nucleic acid comprising a nucleotide sequence as set forth in SEQ ID NO:1 and a nucleic acid comprising a nucleotide sequence as set forth in SEQ ID NO:2 operably linked to a second nucleic acid selected from the group consisting of a heterologous structural gene or antisense DNA.

4. The DNA molecule of claim 3, wherein said first nucleic acid comprises a nucleic acid comprising a nucleotide sequence as set forth in SEQ ID NO:2.

5. The DNA molecule of claim 3, wherein said second nucleic acid is capable of conferring a selected agronomic trait to a plant.

6. The DNA molecule of claim 5 wherein said agronomic trait is herbicide resistance.

7. The DNA molecule of claim 5 wherein said agronomic trait is insect resistance.

8. The DNA molecule of claim 5 wherein said agronomic trait is disease resistance.

9. The DNA molecule of claim 5 wherein said agronomic trait is drought tolerance.

10. The DNA molecule of claim 5 wherein said agronomic trait is salt tolerance.

11. The DNA molecule of claim 5 wherein said agronomic trait is increased yield.

12. The DNA molecule of claim 3, wherein said second nucleic acid encodes a selectable marker.

13. The DNA molecule of claim 3 which further comprises a third nucleic acid selected from the group of an enhancer and an activating element, said third nucleic acid positioned upstream of said first nucleic acid.

14. A transgenic plant cell transformed with DNA comprising the DNA molecule of claim 3.

15. A transgenic plant cell transformed with DNA comprising the DNA molecule of claim 4.

16. A transgenic plant cell transformed with DNA comprising the DNA molecule of claim 5.

17. A transgenic plant cell transformed with DNA comprising the DNA molecule of claim 6.

18. A transgenic plant cell transformed with DNA comprising the DNA molecule of claim 7.

19. A transgenic plant cell transformed with DNA comprising the DNA molecule of claim 8.

20. A transgenic plant cell transformed with DNA comprising the DNA molecule of claim 9.

21. A transgenic plant cell transformed with DNA comprising the DNA molecule of claim 10.

22. A transgenic plant cell transformed with DNA comprising the DNA molecule of claim 11.

23. A transgenic plant cell transformed with DNA comprising the DNA molecule of claim 12.

24. A transgenic plant cell transformed with DNA comprising the DNA molecule of claim 13.

25. A transgenic plant comprising the DNA molecule of claim 3.

26. A transgenic plant comprising the DNA molecule of claim 4.

27. A transgenic plant comprising the DNA molecule of claim 5.

28. A transgenic transformed plant comprising the DNA molecule of claim 6.

29. A transgenic plant comprising the DNA molecule of claim 7.

30. A transgenic plant comprising the DNA molecule of claim 8.

31. A transgenic plant comprising the DNA molecule of claim 9.

32. A transgenic plant comprising the DNA molecule of claim 10.

33. A transgenic plant comprising the DNA molecule of claim 11.

34. A transgenic plant comprising the DNA molecule of claim 12.

35. A transgenic plant comprising the DNA molecule of claim 13.

* * * * *

SEQUENCE LISTING

<160> NUMBER OF SEQ ID NOS: 3

<210> SEQ ID NO 1
<211> LENGTH: 351
<212> TYPE: DNA
<213> ORGANISM: Artificial Sequence
<220> FEATURE:
<223> OTHER INFORMATION: Description of Artificial Sequence:Yeast
      homolog of CaMV 35 S promoter

<400> SEQUENCE: 1

```
tcaaatttttt ctccagttct aaatatccgg aaacctcttg ggatgccatt gcccatctat    60
ctgtaattta ttgacgaaat agacgaaaag gaaggtggct cctataaagc acatcattgc   120
gataacagaa aggccattgt tgaagatacc tctgctgaca ttggtcccca agtggaagca   180 ccacccatg aggagcaccg tggagtaaga agacgttcga gccacgtcga aaaagcaagt    240
gtgttgatgt agtatctcca ttgacgtaag ggatgaacaa caatccaact atccatcgca   300
agaccattgc tctatataag aaagttaata tcatttcgag tggccacgct g            351
```

<210> SEQ ID NO 2
<211> LENGTH: 351
<212> TYPE: DNA
<213> ORGANISM: Artificial Sequence
<220> FEATURE:
<223> OTHER INFORMATION: Description of Artificial Sequence:Yeast
      homolog of CaMV 35S promoter

<400> SEQUENCE: 2

```
tcaaatttttt ctccagttct aaatatccgg aaacctcttg ggatgccatt gcccatctat    60
ctgtaattta ttgacgaaat agacgaaaag gaaggtggct cctataaagc acatcattgc   120
gataacagaa aggccattgt tgaagatacc tctgctgaca ttggtcccca agtggaagca   180 ccacccatg aggagcaccg tggagtaaga agacgttcga gccacgtcga aaaagcaagt    240
gtgttgatgt agtatctcca ttgacgtaag ggatgacgca caatccaact atccatcgca   300
agaccattgc tctatataag aaagttaata tcatttcgag tggccacgct g            351
```

<210> SEQ ID NO 3
<211> LENGTH: 351
<212> TYPE: DNA
<213> ORGANISM: Cauliflower mosaic virus

<400> SEQUENCE: 3

```
tgagactttt caacaaaggg taatatcggg aaacctcctc ggattccatt gcccagctat    60
ctgtcacttc atcaaaagga cagtagaaaa ggaaggtggc acctacaaat gccatcattg   120
cgataaagga aaggctatcg ttcaagatgc ctctgccgac agtggtccca aagatggacc   180
cccacccacg aggagcatcg tggaaaaaga agacgttcca accacgtctt caaagcaagt   240
ggattgatgt catatctcca ctgacgtaag ggatgacgca caatcccact atccttcgca   300
agacccttcc tctatataag gaagttcatt tcatttggag aggacacgct g             351
```